(12) United States Patent
Radermacher et al.

(10) Patent No.: US 9,463,031 B2
(45) Date of Patent: Oct. 11, 2016

(54) DEVICE AND METHOD FOR WORKING MATERIAL

(75) Inventors: Klaus Radermacher, Stolberg (DE); Axel Follmann, Aachen (DE); Stefan Heger, Aachen (DE)

(73) Assignee: MINMAXMEDICAL, Saint Martin D'Uriage (FR)

( * ) Notice: Subject to any disclaimer, the term of this patent is extended or adjusted under 35 U.S.C. 154(b) by 407 days.

(21) Appl. No.: 12/673,187

(22) PCT Filed: Oct. 15, 2008

(86) PCT No.: PCT/EP2008/008699
§ 371 (c)(1),
(2), (4) Date: Mar. 18, 2010

(87) PCT Pub. No.: WO2009/049863
PCT Pub. Date: Apr. 23, 2009

(65) Prior Publication Data
US 2011/0208196 A1    Aug. 25, 2011

(30) Foreign Application Priority Data

Oct. 17, 2007 (DE) .................. 10 2007 050 017

(51) Int. Cl.
*A61B 17/00* (2006.01)
*A61B 17/16* (2006.01)
*A61B 8/08* (2006.01)

(52) U.S. Cl.
CPC .......... *A61B 17/1695* (2013.01); *A61B 8/0808* (2013.01); *Y10T 83/04* (2015.04); *Y10T 83/141* (2015.04)

(58) Field of Classification Search
CPC .............. A61B 17/1695; A61B 17/16; A61B 17/1615
USPC .................. 606/79, 80, 82, 86 R, 96, 102
See application file for complete search history.

(56) References Cited

U.S. PATENT DOCUMENTS

| | | | | |
|---|---|---|---|---|
| 2,401,548 | A * | 6/1946 | Chapman | 606/172 |
| 5,460,182 | A * | 10/1995 | Goodman et al. | 600/342 |
| 6,129,731 | A * | 10/2000 | Haeusler et al. | 606/79 |
| 6,314,312 | B1 * | 11/2001 | Wessels et al. | 600/427 |
| 6,336,931 | B1 * | 1/2002 | Hsu et al. | 606/80 |
| 6,648,904 | B2 * | 11/2003 | Altshuler et al. | 607/96 |
| 7,346,417 | B2 | 3/2008 | Lueth et al. | 700/117 |
| 8,142,365 | B2 * | 3/2012 | Miller | 600/566 |
| 2007/0118135 | A1 * | 5/2007 | Mansmann | 606/80 |
| 2007/0135759 | A1 * | 6/2007 | Kraft et al. | 604/35 |
| 2007/0219602 | A1 * | 9/2007 | Ostrovsky et al. | 607/96 |

FOREIGN PATENT DOCUMENTS

| | | | |
|---|---|---|---|
| DE | 102004035001 | * | 3/2006 |
| WO | WO 2005048852 | | 6/2005 |
| WO | WO 2005048852 A1 | * | 6/2005 |

* cited by examiner

*Primary Examiner* — Kevin T Truong
*Assistant Examiner* — Si Ming Ku
(74) *Attorney, Agent, or Firm* — Blakely Sokoloff Taylor & Zafman LLP

(57) ABSTRACT

The invention relates to a device for working material, in particular for working tissue or bone, comprising a tool head and a tool arranged thereon, wherein the tool head (WK) has at least one support element (2) which is adjustable relative thereto and by means of which the tool head (WK) can be supported on the surface of a material (4) that is to be worked, wherein the position of the tool (1) relative to a material surface to be worked is adjustable through controlled or regulated adjustment of the at least one support element (2) by means of an actuator, depending on data that can be fed to a controlling/regulating unit of the at least one actuator during working of the material.

19 Claims, 2 Drawing Sheets

DEVICE AND METHOD FOR WORKING MATERIAL

CROSS REFERENCE TO RELATED APPLICATIONS

This application is the US-national stage of PCT application PCT/EP2008/008699, filed 15 Oct. 2008, published 23 Apr. 2009 as WO2009/049863, and claiming the priority of German patent application 102007050017.5 itself filed 17 Oct. 2007.

FIELD OF THE INVENTION

The invention relates to an apparatus for working material and comprising a head carrying a tool. The invention further relates to a method of working on material where the tool head with the tool mounted on it is guided along the surface of the material that is to be worked.

BACKGROUND OF THE INVENTION

The described apparatus and method are generally suitable for working on any type of material, here especially tissue or bone, and thus are also usable in medical technology.

When working on materials, especially in medicine and here especially for working on tissue and bone, it is important to have information available about the local properties of the material that is to be worked. For example, in a so-called trepanation, the cranium is opened in order to be able to perform neurosurgical procedures, an osseus access to the interior of the cranium of a living organism, such as for example a human being, being created.

Thus it is the paramount goal to protect the very closely abutting hard meninges, the dura mater, to prevent any type of injury by the tool that is used, as injuries of the dura mater can lead to an extended time for the surgery and also the postoperative healing of the wound, as well as to an increased risk of infection. Beyond that, in the event of an injury of the dura mater, further complications (healing of the wound, mortality and increased treatment costs must be considered.

It is further known in the prior art that for access to the interior of the cranium, special drills are to be used that make several bores along a resection line. These bores can subsequently be connected by an additional instrument or tool, the so-called craniotome, in order to thus create a removable piece of bone. Usually, such a craniotome is a cutting instrument with, for example, a slightly conical cutter with which the cut is made.

It is known to provide the cutter at its drive side with an angled shoe, and to thereby at least theoretically separate it from the dura mater. This shoe serves to protect the dura mater in the area that is to be cut and ensures that the dura mater is continually pushed away from the bone and is thus pushed away from the cutter.

This functional mechanism is known to fail, for example typically in the event of local variations of thickness of the cranial bone, as well as in the case of an adhesion of the dura mater to the cranial bone. Then, tearing of the dura mater can occur in a section that is not visible, as a result of which a direct reaction to this type of damage to the dura mater is not possible, and the damage thus often continues up to the end of the cutting process. During a surgical procedure, such an injury is to be repaired in a targeted manner, for which often the required sutures or duraplastic in addition to a significant extension of the surgical procedure can also be associated with the danger of a liquid fistula and thus the risk of a postoperative infection with a significant increase of mortality, as well as increased costs.

After removing the bone cover, additional surgical steps can be performed and, subsequent to these procedures, the bone cover can, as a rule, be replaced to the extent it is not destroyed by the growth of a tumor, trauma or similar. The cutting technique described above thereby leads to a residual osseous gap, which is the result of a cutting defect because of the bore holes as well as the cutting kerf.

In other medical areas such as, for example, in the mouth, jaw or facial surgery, as well as spinal column surgery, comparable problems result with respect to the protection of the soft tissue.

The subject matter of the invention, i.e. the subsequently described apparatus, as well as the method is, however, not restricted to the use of working on material in medical application areas. The apparatus and method of the type described in the following can be used across the board, in order to be able to work on any type of material, for example, also for working on inanimate bodies, especially hollow forms or two-dimensional structures.

In addition, German patent application DE 101 17 403 [U.S. Pat. No. 7,346,417] also describes a method and an apparatus for controlling material abrasion or working on a material. It is described here how to manually regulate or control a tool depending on the geometry of a specified object volume and a specified object form that is to be obtained with respect to the material abrasion, here, especially the change and the performance of a cutting or drilling tool depending on the navigation coordinates and, for example, then when the targeted object form has been attained, to switch the tool off.

In this type of working of a material it is considered to be disadvantageous, however, when the performance of the tool that is used varies, because of this known method or the known apparatus, it being especially known in the case of cutting or cutting tools that a decrease in performance can under certain circumstances even lead all the way to stopping n a material that is to be worked on, i.e. arresting of the tool in the material. Especially in medical applications, as well as in general in any type of application of working on material, this represents a significant disadvantage, as, at the moment it stops, a tool of this type can get out of control. At best, such a previously known apparatus for working on material can only be used with sufficient safety in this type of processing, if it is based on a rotating operating principle such as, for example, drilling or cutting, not, however, by working by sawing.

OBJECT OF THE INVENTION

The object of the invention is to provide an apparatus as well as a method of working any type of material to be worked for which during the working on the material, automatic control can be applied to position the tool. This is to ensure a precise and especially a safe working of the material, especially in the medical application field, and ensure an especially safe result with any type of material that is being worked.

SUMMARY OF THE INVENTION

This problem is solved to start with by an apparatus of the type described above in which a tool head is provided with at least one support shiftable relative to it and that supports the tool head while the material is being worked on t the surface of a material that is to be worked so that the position of the tool relative to a material surface that is to be worked can be adjusted by controlled or regulated adjustment of the actuator of the support depending on data be fed into a control/regulating unit of the actuator while the material is being worked.

According to the method of the invention, this problem is also solved by the procedure described above in which the position of the tool is adjusted relative to the material surface that is to be worked while the material is being worked by controlled or regulated adjustment of the support provided at the tool head and that provides support relative to the surface of the material that is to be worked so that the adjustment of the support relative to the tool head is dependent on data fed to a control/regulating unit of the actuator of the support while the material is being worked.

Thus the core idea of the invention is to provide an apparatus and a method in which a tool head is used that carries a tool whose position can be influenced by a support on the tool head.

The tool head can to this end be provided with a drive for actuating the tool. Such a drive can, for example, be of the kind that moves the tool or that only supplies a tool with the required energy. Thus, here a tool can be any element or also apparatus suitable for working a material.

In principle, this can be any type of working, such as, for example, separation or also joining, for example, saws, cutters, drills, grinding or milling elements can be used as tools, likewise high-frequency scalpels, cutters and knifes such as also tools or apparatuses that use laser beams or beams of water and tools that are used in adhesion, welding or soldering.

The list of possible tools is fundamentally open to any tool and varies by the desired action on the material, the tool head being adapted to operate the tool that is mounted on it, for which reason, for example, the drive described above or other units can be provided in or on the tool head for operating the tool, be that only for providing it with the required energy.

Further, it is an important aspect of the invention that a tool head carrying a tool is not only guided by external measures such as, for example, purely manually by an operator, or also by a robotic control, but that it is provided here, in accordance with the invention, that at least one adjustable support is provided on the tool head that can be adjusted relative to the tool head and by means of which the tool head is supported or will be supported on the material surface while the material of any type is being worked.

Thus, by means of at least one adjustable support of this type, the distance of the tool head to the surface of the material that is to be worked can be influenced, to which end the support is moved relative to the tool head. For moving the support, at least one actuator is provided in or on the tool head for each of the supports or also perhaps for several of them.

Such an actuator can be operated by a control or regulation unit into which the required data for adjusting the support can be fed while working on the material. Such a unit can be in the tool head, or can also be located externally.

A support of the type mentioned that is mounted on a tool head in addition to a tool can, in a potential and preferred embodiment be designed, for example, as a slide that can be pushed out of or drawn into the tool head by an actuator. Thus, with only one such support in particular the interaction depth of the tool in the material to be worked on during working the material can be selected, for which reason, as described above, data are inputted into the control or regulating actuator.

This way, in a preferred embodiment, more than only one support is provided, for example, two or three or even more supports that can, in particular be configured in such a way that they surround a tool intended for working a material. Thus, in addition to the interaction depth of a tool in the material that is to be worked, the position can also be adjusted with respect to other degrees of freedom, such as, for example, the angles in several directions relative to the material surface, and as a result of the various adjustments of the supports these—with simultaneous abutment of the tool head by means of these supports on the material surface—change the angle of the tool head and thus also the angle of the tool. Precisely this angle adjustment is important in tools with respect to the height adjustment for laser beams or beams of water.

In a different embodiment, the support can also be a sleeve that surrounds a tool. Even in this embodiment, the sleeve-like support can be shifted into and out of the tool head by an actuator. Particularly in rotating tools, such as drills or cutters, such a design of the support can be preferred, while an embodiment with the ram that was mentioned as an example above that supports elements locally separated from the tool can preferably be provided in tools that move without rotation such as, for example, an oscillating motion, as used in the case of sawing tools.

According to a potential embodiment of the method in accordance with the invention, as well as the apparatus, the data, fed during the working process to the actuator of the support are dependent on a specified orientation of the tool head relative to the material that is to be worked.

To determine the orientation the apparatus in accordance with the invention works together with a navigation system that determines the position of the tool head and thus also simultaneously the position of the tool mounted on it relative to a material that is to be worked. If while the material is being worked, the respective position of the tool head is known as the result of such a determination, then corresponding data that depend on position, for example, from a database can be fed to the actuator of the support in order to thus select the position of the tool while the material is being worked.

This way, to determine the position at the tool head and/or at the material, indicia are provided that can be captured by a camera or a different spatial localization system. Hereby, conventional navigation technology can essentially be used.

From the indicia that are captured in an image, for example, for the tool head as well as the material, a conclusion can thus be drawn about the relative position of these two elements with respect to each other, the data from the database being retrieved and stored in a model, for example, prior to working the material by a technique of measurement, in particular image-guided capture, of the material to be worked depending on position.

For this, for example, the data are radiologically captured so that certain properties of the material to be worked can be available in the database depending on position.

The possible properties that should be taken into consideration while working the material and depending on which the data can be captured as a result of this previously mentioned embodiment, or also the embodiments mentioned in the following, can be, for example, the thickness of the material at the location or in the surrounding area of the site where the material is being worked, likewise other properties, such as, for example, in principle, any mechanical property such as dimensions, density or also electrical properties, such as resistances, impedances or any type of property, that could be of interest for the type of working the material.

In a different alternative, or also in addition in an embodiment of the apparatus in accordance with the invention mentioned previously, or the method, the apparatus has at least one sensor unit that captures data for controlling the actuator of the support while the material is being worked.

Thus, it is considered to be important here that in situ, i.e. while working the material with at least one such sensor unit, in particular of a type that is mounted on or in the tool head or on or in the tool itself, the necessary data are captured, whereby these data then represent, for example, information about properties at the site or at least in the surrounding area of the site of the material that is being worked, such as, for example the thickness described above or also other properties.

Thus the possibility exists here that in principle, work on a material can be performed independently of the previous capture of the necessary properties of the material or also in an additional potential embodiment in which both previously mentioned variants are combined, the possibility that the data depending on a determined position of the tool head, that are, for example, from the database described above, are corrected with data that are captured while the material is being worked by a sensor unit on the tool head. For example, in this way the possibility opens up that control of an automatic path-finding by the tool head by means of the data captured directly on or in the surrounding area of the location of the tool can be corrected. Hereby, a higher safety factor can be realized for automatic path-finding.

The sensor unit described above can thereby comprise at least one sensor in order to make it possible to capture a property of the material that is to be worked by using a measurement technique. Hereby, the sensor unit comprises an active element, on account of the action of which first the capture of the certain property is made possible by a measurement technique.

Thus, such a sensor unit can, for example, be based on an acoustic measurement principle and for the execution of a measurement of a desired property, have, for example, an ultrasound sensor and/or an ultrasound receiver. Thus, in one embodiment of the invention there exists the possibility—by means of such a sensor unit that was mentioned—of capturing properties that can be sensed by ultrasound such as, for example, the thickness of the material to be worked at the location or at least in the area surrounding the location of the material to be worked, and by using the thus captured properties build data, that are fed to a control or regulation unit of an actuator of a control element or the several actuator of several control elements in order to determine the position of the tool.

A sensor unit like the one described above, as well as any other possible type of sensor unit for capturing, in principle, any property of a material can basically be located somewhere at the tool head and thus on the apparatus in accordance with the invention. It is important that the possibility exists by means of such a sensor unit that the desired property can be captured at the location or at least in the surrounding area of the location where the material is being worked.

To achieve this, in a preferred embodiment the sensor unit is located at least partially in at least one of the supports, for example, at the end of the support facing the surface of the material that is to be worked. Thus, in particular, when in accordance with the invention, a tool head is supported by at least one such support on the surface of the material that is to be worked, by means of this at least one contact point a measurement for the determination of the property such as, for example, the thickness, can be made.

Here, a complete sensor unit can be located in such a support or only a partial sensor unit so that the capturing of the property can take place by this at least one support alone, or also by the joint working of two sensor parts on different supports.

For example, with a sensor unit that works according to the ultrasound principle, in one of the supports an ultrasound transmitter is located and in another support an ultrasound receiver. Of course, the possibility exists within a support to always mount a complete sensor unit, i.e. in this application case, for example, mount ultrasound transmitters and ultrasound receivers together, where in terms of the process the ultrasound impulses transmitted by the sensor unit of the support can be received by the same sensor unit or by the sensor unit of a different support as echoes.

In this type of ultrasound sensor unit, a sensor unit, in particular a support with such a sensor unit is provided with an applicator for a coupling fluid in order to ensure a better coupling of the ultrasound impulses into the material surface of the material that is to be worked.

In addition to the possibilities mentioned here of using an ultrasound sensor unit, other types of sensor units can of course also be used that employ other measurement systems in order to capture the previously mentioned property such as, for example, the thickness or also other properties such as electric resistances or impedances at the location or in the surrounding area of the location of the material being worked.

With several supports mounted around a tool, data are captured from several sensors that are a part of such a sensor unit and that are then also mounted around the tool so that the measured data of the several sensors can be processed, for example, by a data-processing system in order to draw a conclusion concerning a property at the location of the tool. Thus, for example, the desired properties can be measured at several points around the tool when the tool, for example, is located at a geometric reference point, for example, the central position relative to the location of several sensors that can be in the supports.

In a different potential embodiment the sensor unit is mounted directly on the tool so that the measurement of the desired property can take place directly at the location of the tool with high precision.

In another embodiment the tool head also comprises a sensor unit by means of which data about the navigation can be captured. Such a sensor unit can replace or complement a navigation system of the type described above. For example, as a result of navigation data captured with the sensor unit in or on the tool head, the data of a navigation system that is outside the tool head, for example, of the type described above, are complemented and/or corrected. Such a sensor unit can, for example, comprise at least one inertial sensor that can record acceleration. Thus, for example, the incline and/or also the position of the tool head can be captured. Such a sensor unit can also be an optical sensor that can capture relative motions with respect to the material that is to be worked.

In a further possible embodiment of the apparatus, the data fed to at least one actuator of at least one support, in order to adjust this support relative to the tool head, come from a unit that is mounted outside the tool head and with which a personal sensation of a person can be registered, on whom the apparatus in accordance with the invention for performing the method is being used.

Thus, there exists, for example, the possibility of giving to a person who has been treated a manually operated unit via which the person can communicate the sensation of pain or a sensation of discomfort, for example, by pressing a button. A signal received in this way, for example, depending on the button being pressed can be conveyed to the apparatus in accordance with the invention and here in particular, the control or regulation unit of the actuator in order to ensure that the interaction depth of the tool, for example, is decreased by pushing out the support.

A possible application is, for example, the cutting up of a cast where when sawing a cast having a certain thickness, the skin of the patient that is underneath is protected. At that moment at which a patient feels that a tool splitting the plaster, in particular an oscillating tool such as, for example, an oscillating saw comes in contact or close to the skin of a person, by means of the data fed in as a result of the input of the patient, the support is pushed out at the head, and thereby the interaction depth of the tool in the plaster is decreased.

This type of feedback and availability of data that is provided based on an action by the person for the purpose of controlling the actuator can not only in this example, but in principle, be used for any type of step in which a person who is conscious can thus give feedback.

Each of the various possibilities of the apparatus or the method described above is to be designed, in principle, so that any type of working of material can take place. A particularly preferred application of the method, as well as in particular the apparatus in accordance with the invention can take place when working on material for opening the cranium of a living organism, as here the possibility exists in accordance with the invention to either capture the thickness of the cranial bone by means of a radiological capture of the patient cranium in advance depending on the location, or alternatively or cumulatively control or regulate the thickness of the cranial bone by making the measurements of the sensor unit described above available to the apparatus in accordance with the invention while the cranium is being opened in order to control or regulate the supports.

Other application areas concern, for example, also material abrasion for obtaining uniform thickness of the material along the working path for fundamentally any type of material such as, for example, also metals, plastic or other materials.

BRIEF DESCRIPTION OF THE DRAWING

Embodiments of the invention relating to a medical application are shown in the following figures. Therein.

DETAILED DESCRIPTION OF THE INVENTION

Figure 1:
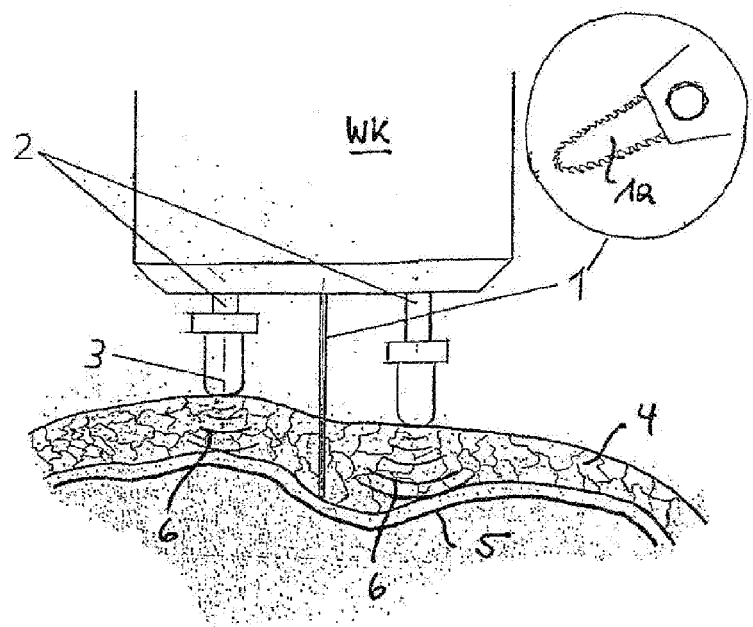
FIG. 1 shows an apparatus in accordance with the invention for the trepanation of a cranial bone.

In a lateral cross section, FIG. 1 shows a tool head WK in accordance with the invention on which is mounted a tool 1 that here is designed as per the explanatory additional illustration as a saw blade 1a in order to thus saw cut into a cranial bone 4 freed of skin on the outside, with a kerf width that corresponds to the thickness of the saw blade.

In order to prevent splitting open the cranial bone during the cutting process, such that dura mater 5 underneath the cranial bone 4 is injured, here according to the invention the tool head carries two supports 2 that flank the saw blade 1 and thus surround the tool 1. The supports 2 are adjustable by unillustrated actuators within the tool head WK and are pushed out of the tool head by these actuators or can be pulled back into the tool head, so that the position of the lower end of each of the supports 2 can be changed.

According to one embodiment, this can be done in that the position of the tool 1 is captured by an external navigation system and the thicknesses of the cranial bone 4 at the location of the tool can be retrieved from a database in order to thus feed the required information to the actuators of the tool head for controlling the supports 2.

In the embodiment illustrated here, which can also be combined with the one that was previously mentioned or can be used alternatively, the supports here have at their lower ends for example sensor units 3 that comprise ultrasound transmitters and ultrasound receivers. The sensor units 3 of lower ends of the supports 2 with which the supports contact the surface of the cranial bone 4 send an ultrasound wave 6, here for example pulsed, that reflects at the inner surface of the cranial bone after running through the thickness of the cranial bone and can be received as echos by the ultrasound receiver of the sensor unit 3.

By knowing the velocity of sound within the cranial bone, the thickness of the cranial bone can be determined at the location of the irradiation of the ultrasound impulses into the cranial bone or also by calculation in the areas between the irradiation sites and preferably at the location of the tool 1. The thus determined thickness information can, if required, be converted into control information for controlling the actuators of the supports 2 in order to thus control with or without feedback the cutting depth of tool 1 into the cranial bone 4. This ensures that an optional safety spacing is left between the lower end of the tool 1 and the dura mater 5 in order to prevent injury of the dura mater 5, while guaranteeing that the cranial bone 4 is completely cut through.

If the thickness of the cranial bone 4 changes as the sawing continues along a desired trajectory at the location of the tool, this is determined in situ by the sensor units 3 in the supports 2, so that by corresponding controlling of the actuators of the supports 2 an additional or smaller projection of the saw blade 1a into the cranial bone 4 can be effected, depending on what thickness of cranial bone is determined at the location of the tool or in its surroundings.

Figure 2:
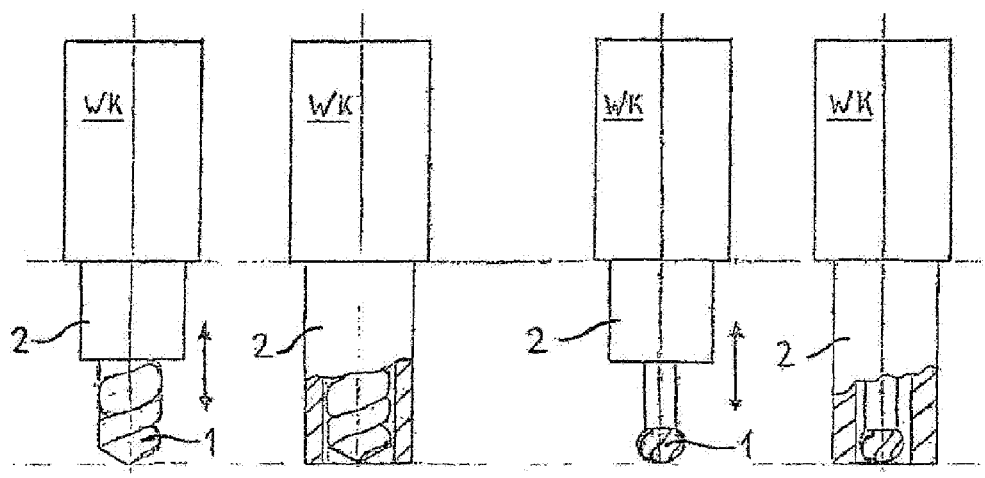
FIG. 2 shows apparatuses in accordance with the invention for making bores or cuts of a desired depth.

FIG. 2 shows different embodiments with a drilling or cutting tool 1. Here the support 2 is a sleeve that fully surrounds the tool 1. How far the driving sleeve 2 projects from the tool head WK determines the spacing between the drill tip or the cutting head tip and the lower end of the sleeve 2 and how far the drill or cutting tool 1 projects into a material that is to be worked.

Here, the sleeve 2 can be pushed all the way out so that the cutting can be completely minimized, as shown in the views on the right of the drill or cutting tools. In practice then, when the lower end of the sleeve 2 bears on the material surface that is to be worked, the drill tool or cutting tool 1 is pulled back out of the material so that the sleeve is pushed all the way out of the tool head. The necessary data can also be supplied here by a controller, e.g. by using navigation data and determined positions relative to the material surface. Likewise, in principle, there is also the possibility that a sensor unit is located in the tool head or in the sleeve, so that, for example, the sleeve can also be used as a wave guide for an ultrasound impulse.

Use as a wave guide also likewise fundamentally applies in the case of an embodiment as in FIG. 1, or generally for any support, so that a sensor unit is not necessarily required to be located within a support, but in the tool head is sufficient, so that then the generated ultrasound impulses or also other measuring signals for the determination of a property of the material are sent out by the supports as signal conductors and likewise, in particular in the case of the acoustic measurement principles, echoes can also be received.

Figure 3:
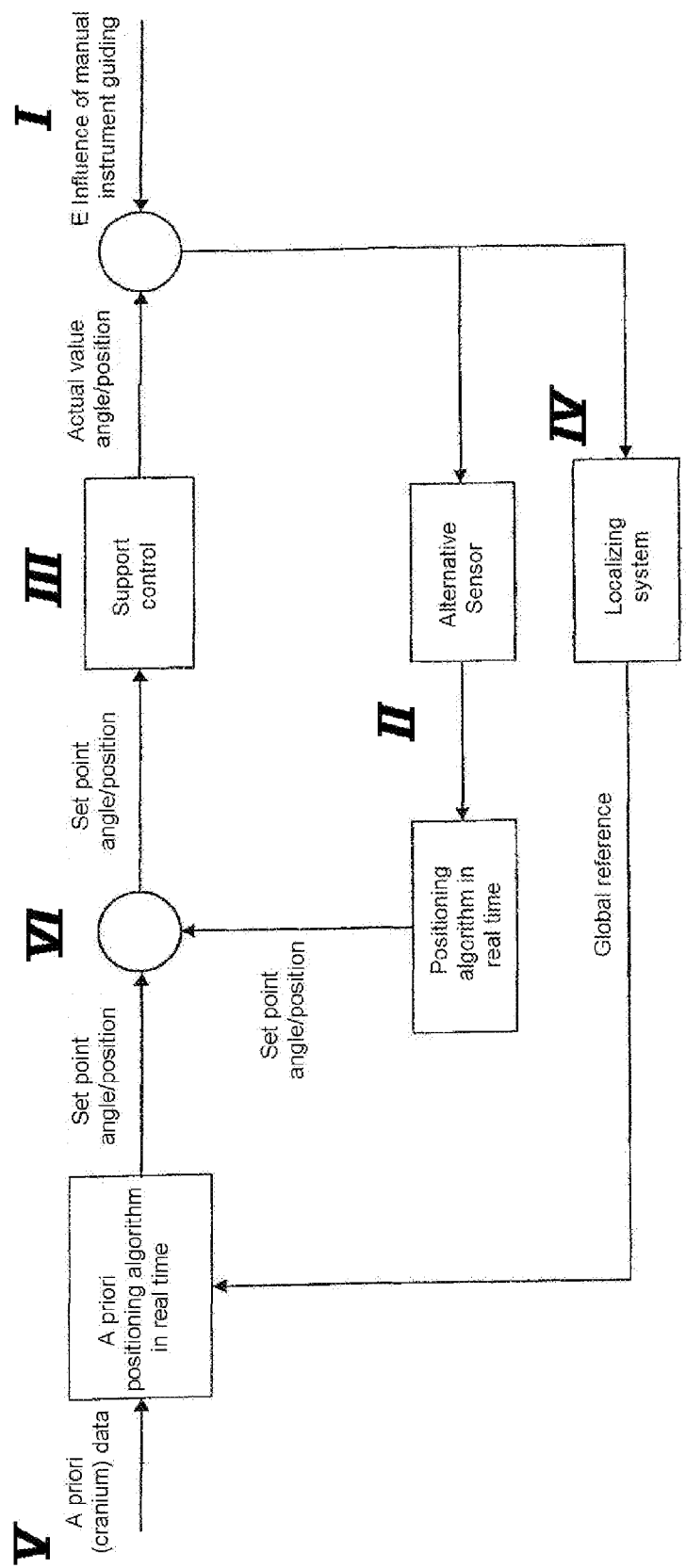
FIG. 3 shows a data-processing schematic.

FIG. 3 schematically shows a possible scheme for executing the method in accordance with the invention on the example of manual guidance of the apparatus in accordance with the invention.

In step I the previous values of the positioning of the apparatus, e.g. relative to the Cartesian coordinates and/or angles can be changed by manually moving the apparatus. In step II, by means of measurements of the sensor unit, new position specifications can be established and adjusted or controlled in step III.

Here, there is also the possibility of a comparison with a localizing system that can determine the position of the apparatus in step IV. Using the determined positions, required data can be added from a database in step V and combined with the data of the sensor unit in step VI. The combined data are then used for controlling the supports with or without feedback.

Concerning all embodiments it is to be noted that the technical characteristics mentioned in connection with the embodiment can be used not only in the specific application, but also in the other embodiments. All revealed technical characteristics of this description of the invention are to be ranked as essential to the invention and are combinable in any way or usable by themselves.

The invention claimed is:

1. An apparatus for working a bone having a surface, the apparatus comprising:
   a tool head;
   a cutting or drilling tool carried on the tool head and adapted to work the surface of the bone along a trajectory on the surface;
   two supports mounted on and shiftable relative to the tool head and each having an end engageable with the surface of the bone being worked and adapted to support the tool head on the surface of the bone being worked at a spacing and at an angle determined by relative positions of the two supports and the tool head;
   respective actuators for shifting each of the two supports relative to the tool head and to the tool for varying the angle and spacing of the tool relative to the surface of the bone being worked;
   a sensor for, while working the bone, collecting data relating to properties of the bone being worked at or around a location where the tool is working the surface of the bone being worked, or data concerning acceleration, angle or position of the tool head relative to the location where the bone is being worked; and
   control means connected to the sensor and to the two actuators, configured for determining, based on data collected by the sensor, at least one property of the bone being worked at or around a location where the tool is working the surface and for computing in real time an adjusted position of each of the two supports relative to the tool head depending on said at least one determined property, the control means further being connected to each actuator for operating the actuators and thereby shifting each of the two supports on the tool head according to the computed adjusted position to adjust a height or angle of the tool relative to the surface of the bone being worked.

2. The apparatus according to claim 1, wherein the two supports flank the tool.

3. The apparatus according to claim 1 wherein the apparatus further comprises:
   navigating means for determining a position of the tool head relative to the bone being worked by means of data from a database.

4. The apparatus according to claim 1, further comprising means for capturing the data prior to working the bone depending on position by measurement techniques and storing the captured data in a database.

5. The apparatus according to claim 1, further comprising a sensor that, while working the bone, captures data or navigation data for controlling the actuator of the support.

6. The apparatus according to claim 5 wherein the sensor is at least partially located in at least one of the two supports or in an end of one of the two supports facing the surface of a bone that is being worked.

7. The apparatus according to claim 5 wherein the sensor is at least partially located in the tool or captures performance data of the tool.

8. The apparatus according to claim 5 wherein the sensor comprises an ultrasound transmitter and an ultrasound receiver.

9. The apparatus according to claim 8 wherein ultrasound impulses transmitted by the sensor on the support are received by the same sensor or the sensor of a different support as echoes.

10. The apparatus according to claim 6 wherein the sensor is provided with means for applying a coupling fluid.

11. The apparatus according to claim 1 wherein the supports each include a slide that is moved out of and into the tool head by the respective actuator.

12. The apparatus according to claim 1 wherein the sensor is located on or in the tool head or on or in the tool such that the captured data represent information about a thickness of the bone at the location or at least in the region surrounding the location of the bone that is being worked.

13. The apparatus according to claim 1 wherein the data is correlated depending on a determined position of the tool head with data captured while the bone is being worked by the sensor on or in the tool head in order to correct an automatic path-finding of the tool head.

14. The apparatus according to claim 12 wherein the data about the thickness is captured by emission of ultrasound impulses' and capturing of ultrasound echoes by the support on tool head.

15. The apparatus according to claim 1 wherein the sensor integrated into the tool head captures navigation data.

16. The apparatus according to claim 1 wherein working of the bone takes the form of leveling, separating or joining.

17. The apparatus according to claim 1 wherein, as the result of working the bone, a cranium of a living organism is opened.

18. An apparatus for working a bone having a surface, the apparatus comprising:
   a tool head;
   a cutting or drilling tool carried on the tool head and adapted to work the surface of the bone along a trajectory on the surface;
   a support mounted on and shiftable relative to the tool head and having an end engageable with the surface of the bone being worked and adapted to support the tool head on the surface of the bone being worked at a spacing determined by relative positions of the support and the tool head;

an actuator for shifting the support relative to the tool head and to the tool for varying the spacing of the tool relative to the surface of the bone being worked;

a sensor for, while working the bone, collecting data relating to properties of the bone being worked at or around a location where the tool is working the surface of the bone being worked, or data concerning acceleration or position of the tool head relative to the location where the bone is being worked; and control means connected to the sensor and to the actuator and configured for determining, based on data collected by the sensor, at least one property of the bone being worked at or around a location where the tool is working the surface and for computing in real time an adjusted position of the support relative to the tool head depending on said at least one determined property, the control means further being connected to the actuator for operating the actuator and thereby shifting the support on the tool head according to the computed adjusted position to adjust a height of the tool relative to the surface of the bone being worked.

19. A method of working a bone having a surface, the method comprising:

guiding a cutting or drilling tool carried on a tool head along a trajectory on the surface of the bone with the tool extending through the surface into the bone and cutting the bone;

engaging two supports shiftable on the tool head with the surface adjacent the tool and thereby supporting the tool on the surface with the two supports at a depth in the bone and at an angle to the surface determined by positions of the two supports relative to the tool head;

detecting with a sensor a thickness of the bone in the immediate vicinity of the tool;

determining, based on data collected by the sensor, at least one property of the bone being worked at or around a location where the tool is working the surface;

computing in real time an adjusted position of each of the two supports relative to the tool head depending on said at least one determined property; and varying the positions of the two supports relative to the tool head in accordance with data derived from the thickness detected by the sensor while the bone is being worked.

* * * * *